US 6,749,570 B2

(12) United States Patent
Üstüner et al.

(10) Patent No.: US 6,749,570 B2
(45) Date of Patent: Jun. 15, 2004

(54) ULTRASOUND METHOD AND APPARATUS FOR IMAGING BREAST

(75) Inventors: Kutay F. Üstüner, Mountain View, CA (US); D-L Donald Liu, Issaquah, WA (US); Thilaka S. Sumanaweera, Los Altos, CA (US)

(73) Assignee: Acuson Corporation, Mountain View, CA (US)

( * ) Notice: Subject to any disclaimer, the term of this patent is extended or adjusted under 35 U.S.C. 154(b) by 70 days.

(21) Appl. No.: 10/227,112

(22) Filed: Aug. 23, 2002

(65) Prior Publication Data

US 2004/0039285 A1 Feb. 26, 2004

(51) Int. Cl.[7] .................................................. A61B 8/00
(52) U.S. Cl. ...................................... 600/443; 128/915
(58) Field of Search ................................. 128/915, 916; 600/443, 437, 444, 448, 449, 407

(56) References Cited

U.S. PATENT DOCUMENTS

| | | | | |
|---|---|---|---|---|
| 4,395,909 A | * | 8/1983 | Steinberg et al. | 73/602 |
| 4,434,799 A | * | 3/1984 | Taenzer | 600/448 |
| 5,840,022 A | * | 11/1998 | Richter | 600/407 |
| 5,938,613 A | * | 8/1999 | Shmulewitz | 600/461 |
| 6,132,375 A | | 10/2000 | Napolitano | |
| 6,368,279 B1 | | 4/2002 | Liu | |

OTHER PUBLICATIONS

M. Krueger et al.; "Limited Angle Ultrasonic Transmission Tomography of the Compressed Female Breast"; *IEEE Ultrasonics Symposium*, pp. 1345–1348; 1998.

Albert Macoyski; "Medical Imaging Systems"; *Prentice–Hall, Inc.*, Englewood Cliffs, New Jersey 07632, pp. 115–129; 1983.

* cited by examiner

*Primary Examiner*—Francis J. Jaworski

(57) ABSTRACT

A method and apparatus for ultrasound breast imaging is described. Breast is positioned in between an ultrasound array and a plate with embedded point or line targets. The apparatus and reflections from the targets are used 1) to improve focusing by correcting for tissue delay and amplitude aberration and 2) to improve diagnostics by constructing speed of sound and attenuation coefficient images.

17 Claims, 3 Drawing Sheets

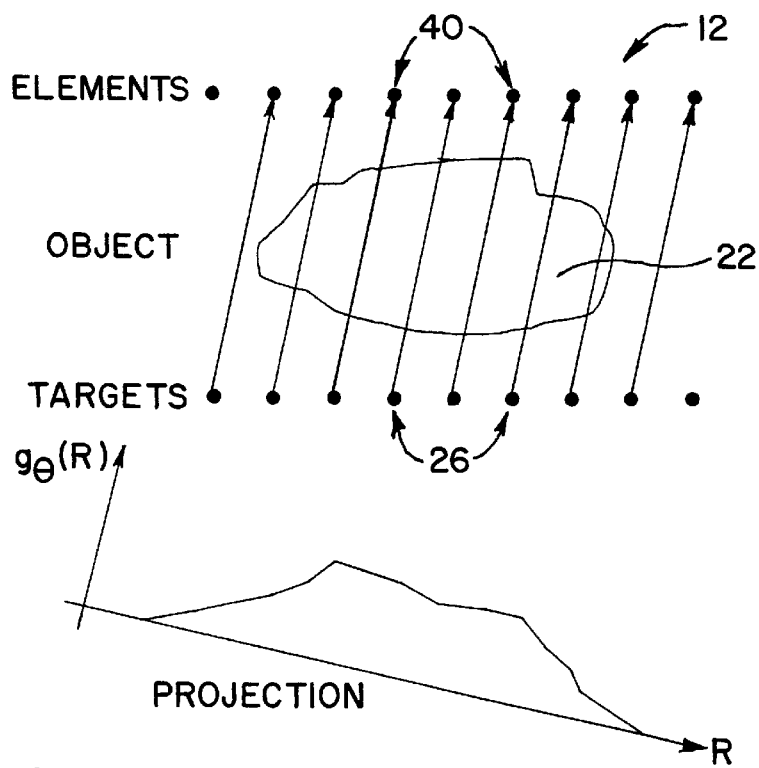
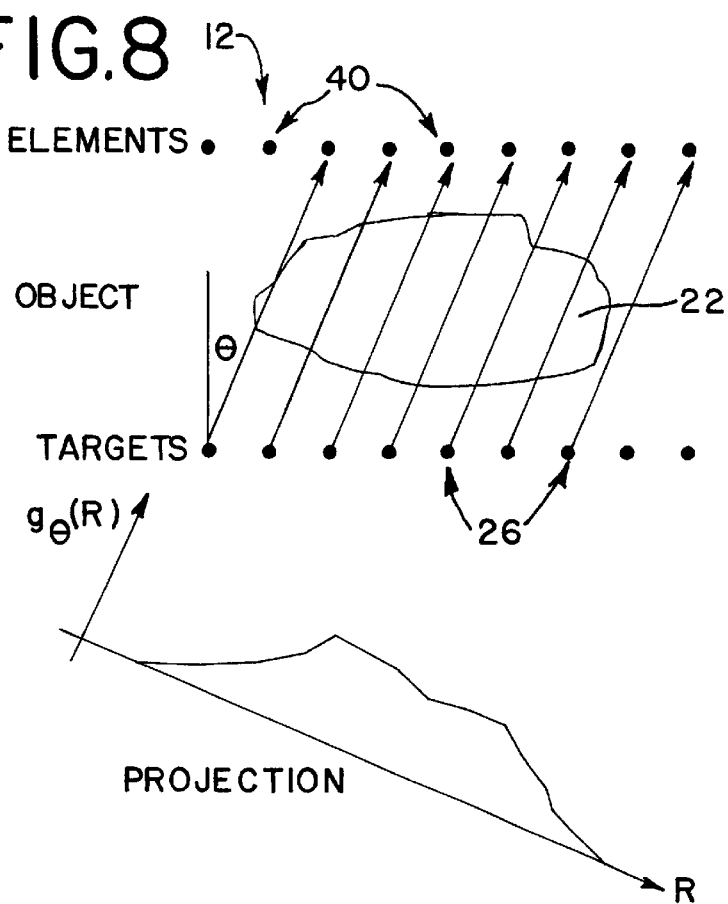

ULTRASOUND METHOD AND APPARATUS FOR IMAGING BREAST

BACKGROUND

This present invention relates to ultrasound imaging of breast tissue. Women with dense breasts may benefit if an ultrasound exam is done in addition to mammogram. In dense breasts with more glandular tissue than fat, ultrasound may help identify malignant masses not visible by mammography. Fatty tissue produces a black mammogram. Dense breasts, on the other hand, produce a predominantly white mammogram. Detecting a small potentially cancerous calcification which maps as a white dot in the mammogram may be difficult. Ultrasound, on the other hand, may depict cancerous spots as black. Black may be easier to detect in a background of dense highly echogenic, and therefore white, glandular tissue.

Mammograms indicate the average density of the tissue along lines of illumination. Two plates are used to compress the breast tissue to increase the sensitivity to local density variations.

Plates have also been used for imaging a breast with ultrasound. Krueger, et al., "Limited Angle Ultrasonic Transmission Tomography Of The Compressed Female Breast," 1998 IEEE Ultrasonics Symposium, pgs 1345–48 use two plates to fix and compress breast tissue. The top plate through which the transducer insonified the breast was made of polyethylene, and the bottom reflection plate was made of stainless steel. The speed of sound through the breast tissue is measured using time-of-flight data between various transmit/receive element pairs of the transducer. A speed of sound image is superposed on top of a B-Mode image. Frequency dependent attenuation coefficients may also be reconstructed using the same set up and radio frequency data.

Many phase aberration techniques have also been used for general ultrasound imaging. Even though some of phase aberration techniques have demonstrated good performance on phantoms with wire or pin targets, the success may be limited in clinical imaging situations. Many of these phase aberration techniques depend on the assumption that the aberration can be modeled as a phase screen in front of the transducer. This assumption may not apply to breast imaging where the aberration is spatially distributed.

BRIEF SUMMARY

A method and apparatus for ultrasound breast imaging is described. A breast is positioned in between an ultrasound array and a plate with embedded point or line targets. The apparatus and reflections from the targets are used 1) to improve focusing by correcting for tissue delay and amplitude aberration and 2) to improve diagnostics by constructing speed of sound and attenuation coefficient images.

The present invention is defined by the following claims, and nothing in this section should be taken as a limitation on those claims. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIGS. 5–8 are graphical representations for determining time-of-flight or attenuation coefficients through transmissions at different angles.

DETAILED DESCRIPTION OF THE PREFERRED EMBODIMENTS

A plate spaced from a transducer by a compressed breast includes a target or multiple targets. The targets are used to determine the time-of-flight or other acoustic property for aberration correction or imaging based on the acoustic property.

The plate has an acoustic impedance as closely matched with the impedance of skin as possible to minimize reflections from the skin-plate interface. The target has an impedance significantly different than the impedance of the plate to maximize the reflections from the targets. The acoustic impedance is given by the product of the speed of sound and density, so any combinations of materials affecting the speed of sound or density may be used for the plate 14 and the target. The attenuation coefficient of the plate is as low as possible to minimize acoustic losses in the plate.

Point or line targets eliminate ambiguity about the location of the point of reflection that affects techniques that use plate reflectors. This is particularly useful in the presence of refraction. Reflection from plate targets is directional, so plate targets provide a very narrow lateral spatial bandwidth. Point targets, on the other hand, are omni-directional and provide a very wide lateral bandwidth. Wide lateral bandwidth is useful for aberration correction. Embedding the targets in an acoustically uniform plate allows easy isolation of the signals of targets from the signals of tissue and the skin/plate interface.

Figure 1:
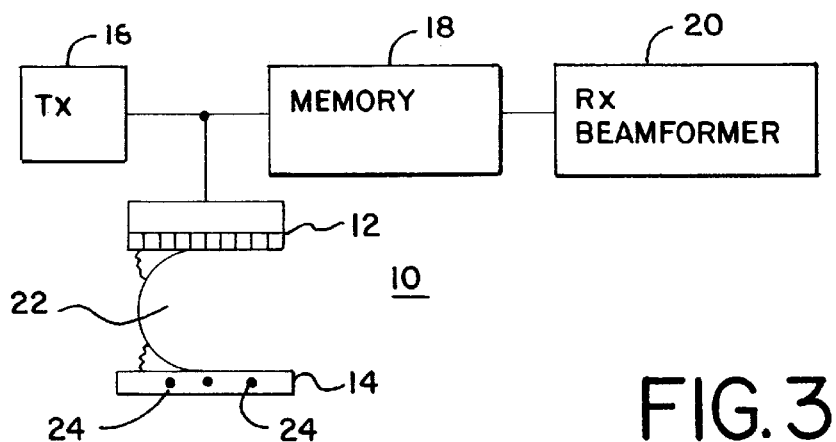
FIG. 1 is a block diagram of one embodiment of a breast imaging apparatus.

FIG. 1 shows an apparatus 10 for ultrasonically scanning breast tissue. The apparatus includes a transducer 12, a plate 14, a transmitter 16, a memory 18 and a receive beamformer 20. Different, additional or fewer components may be provided. For example, additional image processing and display circuitry connects with the receive beamformer 20.

The transducer 12 comprises a 1-D or 2-D array of ceramic, piezoelectric or electromechanical (e.g. cMUT) elements. The transducer 12 is adapted for scanning a three-dimensional volume, but may be adapted for a single scan plane. In one embodiment, the transducer 12 is a 2-D array (i.e. N×M array of elements where N and M are both greater than one) having a planar, concave or curved surface. The surface may be curved for comfortable contact with the breast 22 under compression. In this embodiment, the transducer 12 is placed in contact with the breast 22 through gel but without an intervening plate. The backing material and/or lens of the transducer 12 are operable to withstand the breast compression pressure.

In other embodiments, particularly for 1-D arrays, an intervening low-attenuation plate is provided below the transducer 12. The breast, in this embodiment, is compressed or kept stationary between the plate coupled to the transducer and the plate that houses the targets. The one dimensional array is manually or automatically moved along an elevation dimension for scanning in different scan planes (e.g. three-dimensional imaging). A framework or visible indicators may be provided for marking positions during manual translation. For mechanical translation, a stepper motor is connected to move the transducer 12. A position sensor, such as the known control of the stepper motor, an optical sensor, an electromagnetic sensor, a contact sensor or other sensor, indicates the position of the transducer 12 relative to the apparatus 10, breast tissue or other frame of reference.

The plate 14 is spaced from the transducer 12 such that the breast 12 is positionable between the transducer 12 and the plate 14. The plate 14 comprises a resin, epoxy or other material. The plate 14 conforms to the shape of the breast 22, such as a concave surface operable to be positioned adjacent to the breast 22 during compression. In other embodiments, the plate 14 has a planar surface operable to be positioned adjacent the breast 22. The term "plate" is used to indicate a surface for placement adjacent the breast 22, so the plate may comprise material of any thickness.

Figure 2:
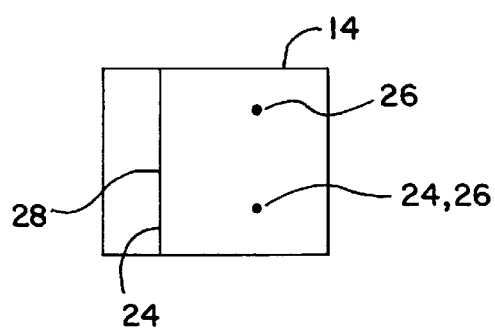
FIG. 2 is a top view of one embodiment of a plate with targets.

The plate 14 includes at least one target 24. As shown in FIG. 2, the targets 24 include a pin or point target 26 and a line target 28, but other targets with greater areas or different shapes may be used in any combination. For example, just point targets 26 or line targets 28 are used. In one embodiment, the point targets 26 are substantially omni directional, such as spherical or semi-spherical with a radius less than the wavelength. The target 24 is metal, air or contrast agent, but other materials may be used. The maximum number of targets is determined by the area of the plate, size of the aperture and the lateral and axial resolution of the transducer. The target 24 is embedded within an interior of the plate 14. In alternative embodiments, part of a line target 28 or the entire target 24 is embedded on a top, bottom or other outer surface of the plate 14. Pin or line targets directly coupled to skin, e.g., with gel, can also be used without a plate housing the targets. This method may not provide a good isolation of the target-skin echo from the skin-air echo or echo from breast tissue. Stabilization of the breast tissue during data acquisition may also be difficult due to lack of compression plates.

The locations of the targets 24 relative to the elements of the transducer 12 are used to assist tissue aberration correction and refraction correction. A step motor for controlling compression of the breast 22 between the plate 14 and the transducer 12 provides information about the distance between the plate 14 and the transducer 12. In alternative embodiments, an optical sensor, electromagnetic sensor, user measurement or other sensor provides the distance information. In combination with the sensed or known position of the elements of the transducer 12 and the known placement of the targets 24 within the plate 14, the distance, angle or other location information of a line of travel between a target 24 and any element of the transducer 12 is calculated. In one embodiment, the position of targets 24 relative to the transducer 12 are determined from ultrasound data. Since the position of the targets 24 are known, the position or sweep speed of the transducer 12 is determined from the ultrasound data.

The transmitter 16 comprises a waveform generator or a transmit beamformer. The transmitter 16 is operable to relatively delay and apodize waveforms for different elements of the transducer 12 for steering and focusing transmission of ultrasound energy. Alternatively, the transmitter 16 is operable to provide a transmit waveform to a selectable, single element or group of elements of the transducer 12.

The memory 18 comprises any of various now known or later developed memory devices, such as a random access memory. After amplification, filtering, analog-to-digital conversion and other receive processing of signals from the elements of the transducer 12, the memory 18 stores radio frequency, intermediate frequency, base band frequency or other data separately representing the signals at each of the elements of the transducer 12. The aperture or element positions associated with the data are also stored in the memory 18. The memory 18 allows for non-real time processing of the stored information, such as processing the information seconds, minutes, hours or days after acquisition. In alternative embodiments, real time processing is provided with or without the memory 18.

The receive beamformer 20 comprises a plurality of delays, a plurality of amplifiers and an adder for focusing and apodizing the received signals. Filters, memory, processors and other digital or analog components may be provided for determining time-of-flight, attenuation coefficient, an acoustic characteristic, aberration correction or other information. The receive beamformer 20 is operable to generate an ultrasound image based on the received signals from the transducer 12 or the memory 18. The receive beamformer 20 is also operable to process single element information for aberration correction and imaging based on time-of-flight, attenuation coefficients or other acoustic characteristics.

In one embodiment, the transmitter 16, memory 18 and receive beamformer 20 comprise a Siemens Sonoline™ Elegra or Acuson—A Siemens Company Sequoia® ultrasound system with transmit and receive beamformers operable with a single element or a larger aperture at a given time. For example, a single element is used to scan an aperture of the array using B-mode based scanning. One element is used for transmitting and an off-set single element is used for receiving. The transmit and receive element pairing is shifted across the aperture of the transducer 12 to acquire a plurality of frames of data. The offset used is zero (same element for both transmit and receive) or greater. A plurality of scans with different offsets may be obtained, such as using offsets of 0, 2, 4, 6, . . . for each of a plurality of different transmit elements.

Figure 3:
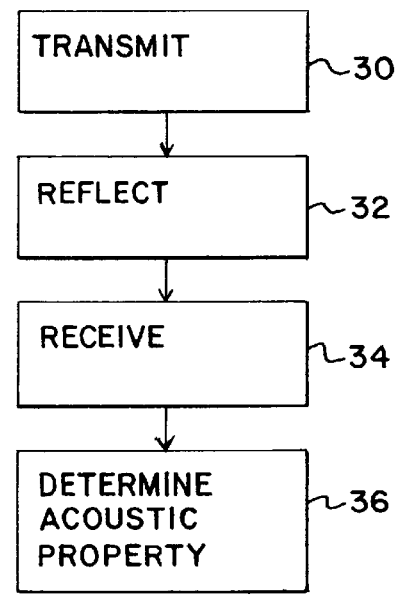
FIG. 3 is a flow chart diagram of one embodiment of a method for determining acoustic properties for breast imaging.

FIG. 3 shows a method of one embodiment for ultrasonically scanning breast tissue using the apparatus 10 of FIG. 1. In general, the breast 22 is compressed between the transducer 12 and the bottom plate 14 with enough compression to keep the breast stationary during the data acquisition and imaging. The breast 22 is insonified and echoes from the targets 24 are analyzed. Brightness variations, such as due to the attenuation, $\alpha$, of the breast, or delay differences given the known distance of travel to and from a target 24 indicates an area of the breast 22 with an amplitude or delay aberration. The aberration is then corrected for ultrasound imaging or identified as a possible area of further examination, such as by generating an image based on the acoustic characteristic (e.g. time-of-flight or attenuation coefficient).

In act 30, ultrasonic energy is transmitted from the transducer 12. For example, a short (e.g. 1–3 cycle) pulse is transmitted from a single element. Longer or shorter pulses may be used. Two or more elements may be used for a given transmit event to provide focus or without focus.

At least some of the ultrasonic energy propagates through the breast 22 and into the plate 14. In act 32, some of this ultrasonic energy reflects from the targets 24 within the plate 14. Where the targets are point, line, spherical or not a plate, the reflected ultrasonic energy propagates back through the plate 14 and breast 22 in a plurality of directions.

Figure 4:
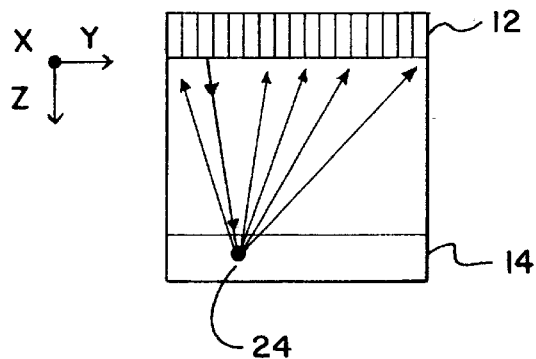
FIG. 4 is a graphical representation of one embodiment of reflecting acoustic energy from a target embedded in a plate.

In act 34, the reflected ultrasonic energy is received by one or more elements of the transducer 12. For example, all or a sub-set of two or more of the elements are used to receive the reflected ultrasound at different offsets from the transmit element as shown in FIG. 4. A time period associated with the expected two-way time-of-flight is used to identify the acoustic energy reflected from one or more targets 24. Acoustic energy reflected from the breast 22 may also be identified or stored for imaging. Where a plate or other medium is provided between the transducer 12 and the breast 22, the properties of the medium is accounted for in identifying acoustic properties of the received reflected signals from the breast.

In act 36, an acoustic property of the received signals is determined. Any of attenuation coefficient, time-of-flight or other property may be determined. The property is used for other types of imaging, such as for aberration correction of B-mode or Doppler imaging. Alternatively or additionally, the property is used as detected information to directly form an image. For example, a two or three-dimensional image based on time-of-flight or attenuation coefficient information is overlaid on a B-mode image.

In one embodiment, the time-of-flight and/or attenuation information is used to determine aberration corrections. One or both of delay and amplitude profiles may be determined for correcting the effects of aberrations. Differences in time-of-travel or attenuation as a function of propagation path relative to any given focal point and element of the transducer 12 are applied to the transmit and/or the receive delays and apodization. Various methods now known or later developed can be used for calculating the aberration corrections. In one embodiment, the apparatus 10 is calibrated, data is acquired and the aberration corrections for subsequent transmissions or receptions are calculated. Other processes may be used, such as not using calibration.

For calibration, a uniform medium of known acoustic properties and thickness (e.g., another plate, water, etc.) is placed in between the transducer 12 and the target plate 14. If the targets 24 are embedded within the plate 14, the calibration may be performed without an additional medium in between the transducer 12 and the target plate 14. Acoustic energy is sequentially transmitted from and received by each element. The received echo signals from the surface of the target plate 14 are stored. If there is no medium between the transducer 12 and the plate 14, the received echo signals from one or more targets 24 within the plate 14 are stored.

The delay and amplitude calibration values are determined from the stored signals for each transmit and receive channel. The delay and amplitude calibration values compensate for the defocusing effects of the transducer's 12 element-to-element delay and amplitude variations and the system's (e.g. the transmitter and receiver analog signal paths) channel-to-channel delay and amplitude variations. The peak amplitude and delay of the envelope of data for each element or channel is used to determine the roundtrip (transmit and receive) amplitude and delay calibration values for the total signal path. Alternatively, the amplitude of a particular spectral component is used to determine the amplitude and delay information.

The calibration delay and amplitude values are applied for subsequent use of the apparatus 10. The delay and amplitude calibration values are applied at the delay and apodization stages of the transmitter 16 and receive beamformer 20. The calibration values are separated into time and amplitude for each element. Alternatively, only time is calibrated, only amplitude is calibrated, or the time and amplitude is combined and applied collectively depending on the complexity of the implementation.

The coordinates of the targets 24 relative to the elements of the transducer 12 may also be calibrated to account for any variability in the manufacturing of the target plates 14. The location of a target 24 can be determined by sequentially firing each element in the array and receiving on the same element. The elevation and azimuth coordinates of the element with the least delayed target echo indicate the elevation and azimuth coordinates of the target. Alternatively a volume scan, or a C scan image of the target plane, can be used to map the positions of all the targets.

The calibration is performed once for an apparatus 10, such as at a manufacturing facility. Calibration may also be repeated occasionally or prior to each use.

After calibration, data is acquired. Acoustic energy is transmitted from a single element. Alternatively, acoustic energy is transmitted from a sub-aperture of elements focused on one of the targets 24. The width of the sub-aperture is selected to be comparable to a likely correlation length of any aberrator. The correlation length is given by the width of the autocorrelation function of the aberrator, more specifically, the width at which the autocorrelation function falls below 0.2 or another value of the autocorrelation peak. If the delay and amplitude aberrations have different correlation lengths, the correlation length of the more dominant expected aberration parameter, which is the delay for most applications, is used as a reference. Alternatively, a beam of acoustic energy is transmitted from a full aperture focused on one of the targets 24 to increase the signal-to-noise ratio (SNR) and improve the isolation of echoes from that particular target 24. In yet another alternative, a plane wave is transmitted, reflected energy is received with all or a sub-set of the elements, and the aberration is estimated from data of all or a sub-set of the insonified targets 24. Using plane wave insonification reduces the ability to isolate echoes from adjacent targets 24.

Using a temporal window, the echoes from tissue and the tissue-plate 14 interfaces are removed, or the received signals from the targets 24 are isolated. Preferably, the receive delays determined based on the distance of the target 24 and an assumed constant speed of sound are applied before this temporal windowing. The isolated receive signals from the target 24 for multiple or all of the elements (i.e. receive channels) are stored.

The delay and amplitude aberration corrections are determined from the elapsed time-of-flight or peak amplitude of the reflected ultrasonic energy from the target 24. A frequency spectrum may be determined for frequency specific aberration effects on the reflected ultrasonic energy from the target 24.

An integrated delay aberration profile, $\tau_f(x_i, y_j, 0| x_k, y_l, z_t)$ is estimated where $(x_i, y_j, 0)$ is the array element location, $(x_k, y_l, z_t)$ is the point target 26 location, $z_t$ is the depth of the point target 26, and $\tau_f$ is the integral of the delay errors over the line connecting the respective array element and the point target 26. The refraction is assumed to be negligible. To estimate $\tau_f$, signals from each adjacent channel pair (i.e. received signals from adjacent elements) are cross-correlated. The delays at which the cross correlation functions peak as a function of element position determines the delay aberration profile. Alternatively, the method described in U.S. Pat. No. 6,368,279, the disclosure of which is incorporated herein by reference, is used. Other delay aberration profile calculation processes may be used.

An integrated amplitude aberration profile, $\alpha_I(x_i, y_j, 0| x_k, y_l, z_t)$ is estimated. $\alpha_I$ is the peak of the envelope amplitude or the amplitude of a particular spectral component of the target echo at each channel or element.

The integrated delay and amplitude aberration profiles are corrected for differences in speed of sound and attenuation coefficient between the target plate 14 and typical breast tissue. This is to compensate for different amounts of delay and attenuation each pulse-echo received at different channels or elements have experienced due to different propagation distances inside the target plate. These differences are accounted for in the profiles. Optionally, $\tau_I$ and $\alpha_I$ are low pass filtered to reduce noise in the profiles.

The integrated aberration profiles are used to determine the aberration correction profiles for a particular target location. In one embodiment, aberration correction profiles are determined using one transmit element, one target and a plurality of receive elements for each scan line to be used for imaging. Alternatively, more than one target or more than one transmission is used to determine the aberration correction profiles for a given scan line.

To determine aberration correction profiles along the line $(x_k, y_l, z)$ at an arbitrary depth $z<z_t$, the integrated aberration profiles can be scaled by a scalar $z/z_t$ (i.e. no correction at zero depth and full correction at the target depth). Alternatively, a non-linear depth dependent aberration scalar may be used. These approaches assume that aberration in the breast is cumulative with depth. The above technique of determining aberration correction profile for arbitrary depths through scaling of an integrated aberration estimation from a single target can be improved by using integrated aberration estimations from multiple point targets. The aperture overlap in the integrated aberration estimate profiles from multiple targets can be used to determine the correction terms for depths shallower than the targets' depth, much like the speed of sound reconstruction technique described by Kruger et al. Alternatively, an interpolation scheme combines delay profiles estimated using different targets 24. For example, if the delay correction for a particular element is determined to be $T_A$ using target A, and $T_B$ using target B, then, for lateral positions between points A and B along the same depth, a linearly interpolated delay value $(1-x)T_A+xT_B$ is used, where x varies between 0 and 1 as the position moves between A and B. Furthermore, a nonlinear interpolation such as $(1-f(x))T_A+f(x)T_B$ (where $0 \le f(x) \le 1$ for $0 \le x \le 1$) may be used to make the spatial transition more smooth. If a derived delay correction profile is spatially limited due to element directivity or SNR, it will be zero-padded or otherwise continuously extended to cover the whole array before interpolation. After delay profiles have been determined for all lateral positions at the same depth, they can be scaled down for use at shallower depths, as noted above. The scaling factor may be the depth factor $z/z_t$ itself, or a nonlinear function $g(z/z_t)$ of the depth factor.

For generating an image with the transducer as a function of the aberration corrections, the amplitude and delay aberration corrections for a given scan line are selected for one or more focal depths. For receive operation, delay and amplitude aberration corrections are dynamically updated as a function depth. In alternative embodiments, a single delay or amplitude aberration correction is applied for receiving along a scan line. In yet other alternative embodiments, only one of or none of amplitude or delay aberration corrections are applied for one or both of transmit and receive operations.

Figure 5:
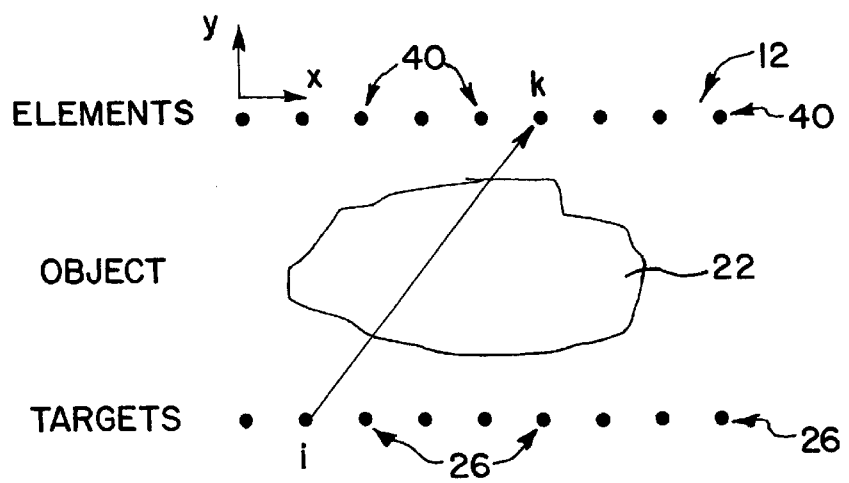

In an additional or alternative embodiment, a speed of sound image is generated as a function of the time-of-flight or elapsed time for the reflection from a target. For example, the acoustic property images taught by Krueger et al. are used. FIG. 5 shows an object, such as breast tissue 22 between the array elements 40 and a plurality of point targets 26. Using the signal received by the $k^{th}$ element, the integral of the speed of sound distribution and the integral of the attenuation distribution along the line connecting the $i^{th}$ target and the $k^{th}$ element is measured. The integral is represented by:

$$g_{ik} = \int_{l_{ik}} f(x, y) dl$$

where $f(x, y)$ is the speed of sound distribution or the attenuation distribution and $g_{ik}$ is the integral of $f(x, y)$ along the line $l_{ik}$.

Figure 6:
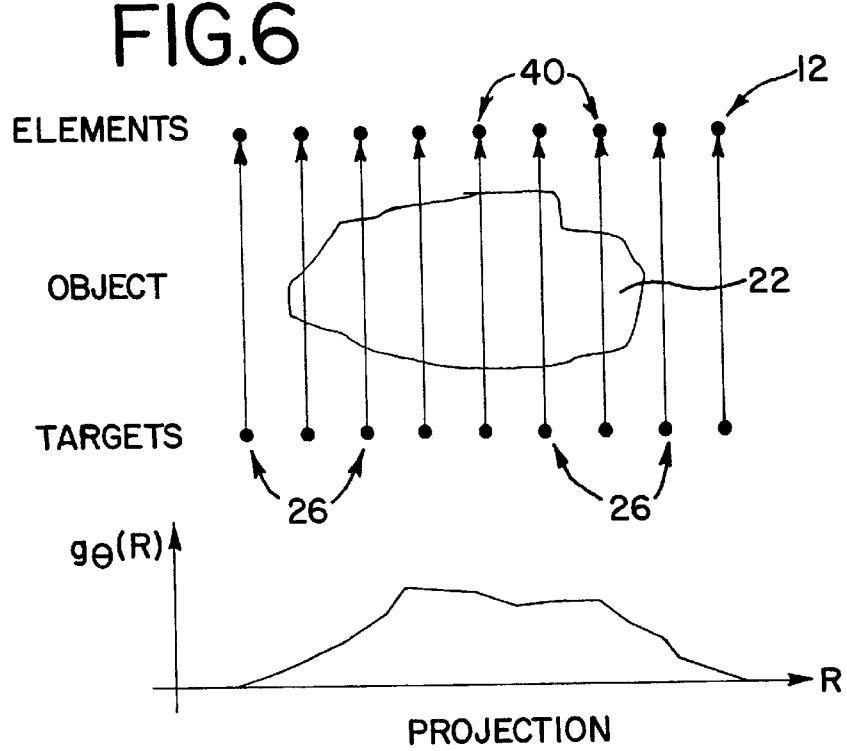

FIGS. 6–8 shows the projection of $f(x, y)$, measured at different angles. The following equation shows the projection of $f(x, y)$, $g_\theta(R)$, at an angle $\theta$:

$$g_\theta(R) = \iint f(x, y) \delta(x \cos \theta + y \sin \theta - R) dx dy$$

If these projections are collected for all $\theta \in [0, \pi)$, the original distribution, $f(x, y)$ can be reconstructed using a number of known techniques. Inverse Fourier transform (2-D), back projection and filtered back projection are a number of such techniques. Such techniques are used in Computed Tomography (CT) and Magnetic Resonance Imaging (MRI). For example, the fan-beam projection geometry found in some CT scanners, where a source is fixed at center and the receivers are lined up along an arc or a straight line, closely mimics the geometry of receiving echoes from a point target, so a similar reconstruction algorithm can be used to recover sound speed and/or attenuation coefficient distribution using time-delay and amplitude information.

In the embodiment shown in FIGS. 5–8, projections for less than all angles are available. Projections for about 90 degrees may be possible. Reconstructing $f(x, y)$, approximately using back projection or filtered back projection may be done with a limited number of back projections. In back projection, $g_\theta(R)$, is uniformly "spread" for all pixels along the line given by:

$$x \cos \theta + y \sin \theta = R$$

After "spreading" the values of $g_\theta(R)$, the object is reconstructed by adding the "spreaded" values. In filtered back projection, $g_\theta(R)$, are spread with weights.

$g_\theta(R)$ may be measured using a variety of methods. In a first example, acoustic energy is transmitted from a single element 40 and received with all or a plurality of elements 40. Using time delays, the $k^{th}$ receive element 40 can separate the signal reflected by the $i^{th}$ target. Subtracting half the measured delay integral or attenuation integral at $k^{th}$ receive element 40 from the measured delay integral or attenuation integral at the $j^{th}$ receive element 40, $g_{ik}$ may be estimated, and hence $g_\theta(R)$. As a second example, energy is transmitted from a sub-array of elements 40 focused on the $i^{th}$ target 26, and echoes are received by multiple elements 40. The measurement of $g_{ik}$ is straightforward. Due to focusing on transmit, the signal-to-noise ratio (SNR) can be improved over the first example above. In a third example, energy is transmitted from a sub-array of elements 40 focused on the $i^{th}$ target 26, and echoes are received by multiple focused sub-arrays. The measurement of $g_{ik}$ is similar to the second example above, except, the resolution of R is now lower. Due to focusing on receive, the SNR can further be improved over the second example. Other measurements may be provided using any combination of focused or unfocused receive or transmit sequences. Back projections and filtered back projections along wavefronts after one or more reflections may also used.

While the invention has been described above by reference to various embodiments, it should be understood that many changes and modifications can be made without departing from the scope of the invention. For example, any of various materials now known or later developed may be used for the targets or plate. Other processes may be provided, such as the synthetic elevation aperture processes of U.S. Pat. No. 6,132,375, the disclosure of which is incorporated herein by reference.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. An apparatus for ultrasonically scanning breast tissue, the apparatus comprising:

a transducer;

a plate spaced from the transducer such that a breast is positionable between the transducer and the plate, the plate comprising a material operable to allow propagation of ultrasound energy and at least one target, the at least one target having an acoustic impedance different than the material.

2. The apparatus of claim 1 wherein the at least one target is more operable to reflect acoustic energy than the material.

3. The apparatus of claim 1 wherein the transducer comprises a 2-D array with a planar surface.

4. The apparatus of claim 1 wherein the transducer comprises a 2-D array with a concave surface.

5. The apparatus of claim 1 wherein the plate comprises a planar surface operable to be positioned adjacent the breast.

6. The apparatus of claim 1 wherein the plate comprises a concave surface operable to be positioned adjacent the breast.

7. The apparatus of claim 1 wherein the at least one target comprises a point target.

8. The apparatus of claim 1 wherein the at least one target comprises a line target.

9. The apparatus of claim 1 wherein the at least one target is embedded within an interior of the plate.

10. The apparatus of claim 1 wherein the at least one target is embedded on a surface of the plate.

11. A method for ultrasonically scanning breast tissue, the method comprising:

(a) transmitting ultrasonic energy from a transducer;

(b) reflecting the ultrasonic energy from at least one target on or within a plate, the plate spaced from the transducer such that a breast is positionable between the transducer and the plate; and (c) receiving the reflected ultrasonic energy at the transducer.

12. The method of claim 11 wherein (a) comprises transmitting a pulse from at least one element of the transducer and (c) comprises receiving the reflected ultrasonic energy with the at least one element.

13. The method of claim 11 further comprising:

(d) determining an elapsed time between (a) and (c).

14. The method of claim 11 further comprising:

(d) determining a peak amplitude of the reflected ultrasonic energy from the at least one target.

15. The method of claim 11 further comprising:

(d) determining a phase at a selected temporal frequency of the reflected ultrasonic energy from the at least one target.

16. The method of claim 11 further comprising:

(d) determining aberration corrections in response to (c); and (e) generating an image with the transducer as a function of the aberration corrections.

17. The method of claim 13 further comprising:

(d) generating a speed of sound image as a function of (d).

* * * * *